United States Patent [19]

Abou-Gharbia et al.

[11] Patent Number: 4,882,432
[45] Date of Patent: Nov. 21, 1989

[54] POLYCYCLIC-CARBAMIC ACID PIPERAZINOALKYL ESTERS AND AMIDES

[75] Inventors: Magid A. Abou-Gharbia; John P. Yardley, both of Gulph Mills; Wayne E. Childers, Jr., Yardley, all of Pa.

[73] Assignee: American Home Products Corporation, New York, N.Y.

[21] Appl. No.: 294,853

[22] Filed: Jan. 9, 1989

[51] Int. Cl.$^4$ .................. C07D 403/04; C07D 241/04
[52] U.S. Cl. ................................ 544/295; 544/357; 544/360; 544/380; 544/393; 544/400
[58] Field of Search ............... 544/295, 357, 360, 380, 544/393, 400

[56] References Cited

U.S. PATENT DOCUMENTS

| | | | |
|---|---|---|---|
| 4,001,223 | 1/1977 | Sugimoto et al. | 544/380 |
| 4,202,898 | 5/1980 | Depoortere | 544/394 |
| 4,510,140 | 4/1985 | Nardi et al. | 544/360 |
| 4,605,655 | 8/1986 | Yevich et al. | 544/295 |

FOREIGN PATENT DOCUMENTS 7017031  5/1971  Netherlands .

OTHER PUBLICATIONS

Derwent Abstract 85000957/01–German Patent No. 3321-969.
Derwent Abstract No. 87–049798/07–U.S. Pat. No. 4,640,921.
Barone et al., Drug Clin. Pharm., 20,770, 1986.

*Primary Examiner*—Glennon H. Hollrah
*Assistant Examiner*—James H. Turnipseed
*Attorney, Agent, or Firm*—Richard K. Jackson

[57] ABSTRACT

The compounds of the formula:

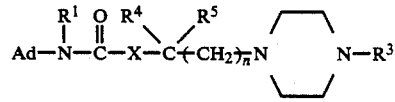

wherein Ad is 1-adamantyl, 2-adamantyl or 3-noradamantyl; X is —O— or

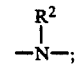

n is 1,2,3 or 4; $R^1$ and $R^2$ are, independently, hydrogen, alkyl, phenyl, benzyl, or substituted phenyl or benzyl in which the substituent is alkyl, alkoxy, halo, cyano, nitro or trifluoromethyl; and $R^3$ is phenyl, benzyl or substituted phenyl or benzyl in which the substituent is alkyl, alkoxy, halo, nitro, cyano or perhalomethyl, 2-, 3-, or 4-pyridinyl, 2-, 4-or 5-pyrimidiny; or 2- or 3-pyrazinyl; $R^4$ and $R^5$ are independently, hydrogen, methyl, phenyl or benzyl; or a pharmaceutically acceptable salt thereof, are useful anxiolytic/antidepressant agents, with elements of antipsychotic activity.

8 Claims, No Drawings

POLYCYCLIC-CARBAMIC ACID PIPERAZINOALKYL ESTERS AND AMIDES

BACKGROUND OF THE INVENTION

Derwent Abstract 85-000957/01 of German Application 3,321,969 discloses 1-pyrimidyl-4-substituted piperazine derivatives which possess a broad variety of CNS activity including anxiolytic and antidepressant properties. Netherlands Pat. No. 7,017,031 discloses 8-(heteroarylpiperazinylalkyl)-8-azaspiro[4,5]decane-7,9-diones as tranquilizers. U.S. Pat. No. 4,640,921 (Derwent Abstract 87-049798/07) discloses the use of the buspirones of the Netherlands patent in the treatment of sexual dysfunction in anxious patients. The anxiolytic activity of buspirone-like compounds has been attributed to their selective activity at the serotonin (5-hydroxytryptamine; 5-HT) subtype receptor designated the $5\text{-HT}_{1A}$ receptor. U.S. Pat. No. 4,202,898 discloses the treatment of anxiety and depression with aromatically substituted piperazine derivatives. $5\text{-HT}_2$ antagonists, such as Ritanserin, lack $5\text{-HT}_{1A}$ affinity but demonstrate clinical efficacy as anxiolytic-antidepressant agents (Barone et al., Drug Clin. Pharm., 20, 770, 1986).

DESCRIPTION OF THE INVENTION

In accordance with this invention there is provided a group of novel compounds, some of which exhibit selective serotonin $5\text{HT}_{1A}$ receptor affinity which characterizes them as antidepressants and anxiolytics; some of which exhibit both $5\text{HT}_{1A}$ receptor affinity and dopamine D2 receptor binding which characterizes them as anxiolytic/antidepressant agents with elements of antipsychotic activity. The compounds of this invention are of the following structural formula:

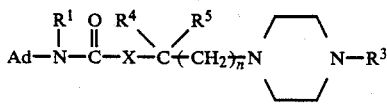

wherein
Ad is 1-adamantyl, 2-adamantyl, or 3-noradamantyl;
X is —O— or

n is 1, 2, 3 or 4;
$R^1$ and $R^2$ are, independently, hydrogen, alkyl of 1 to 3 carbon atoms, phenyl, benzyl, or substituted phenyl or benzyl in which the substituent is alkyl of 1 to 3 carbon atoms, alkoxy of 1 to 3 carbon atoms, halo, cyano, nitro or trifluoromethyl;
$R^3$ phenyl, benzyl or substituted phenyl or benzyl in which the substituent is alkyl of 1 to 3 carbon atoms, alkoxy of 1 to 3 carbon atoms, halo, nitro, cyano or perhalomethyl, 2-, 3-, or 4-pyridinyl, 2-, 4- or 5-pyrimidinyl or 2- or 3-pyrazinyl;
and
$R^4$ and $R^5$ are, independently, hydrogen, methyl, phenyl or benzyl; or a pharmaceutically acceptable salt thereof.

The pharmaceutically acceptable salts are conveniently derived by conventional means from such acids as hydrochloric, hydrobromic, sulfuric, phosphoric, methane sulfonic, nitric, p-toluene sulfonic, acetic, citric, maleic, succinic acid, and the like. The halogens embraced by the term halo are chlorine, bromine, iodine and fluorine, preferably chlorine, bromine or fluorine. The preferred compounds are those derived from 1-adamantanamine.

The compounds of this invention may be prepared by a variety of synthetic routes using conventional methods. For instance, the appropriate aromatically or heteroaromatically substituted piperazine may be conveniently reacted with the appropriately substituted

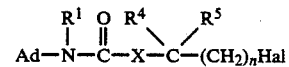

in DMF in the presence of an acid acceptor such as triethylamine or cesium carbonate. Alternatively, an isocyanate of noradamantan-3-amine or 1-adamantanamine may be prepared by refluxing with trichloromethyl chloroformate in $CH_2Cl_2$ and the presence of a suitable base, such as triethylamine, followed by reacting the intermediate isocyanate with the desired aromatically or heteroaromatically substituted piperazinyl alkylamine or alkylhydroxy intermediate to obtain the desired urea or carbamate, respectively.

The following examples illustrate, without limitation, the specific methods employed in production of a representative number of compounds embraced by this invention.

EXAMPLE 1

N-[2-[4-(2-pyrimidyl)-1-piperazinyl]ethyl]-N'-tricyclo[3.3.1.1(3,7)]dec-1-ylurea To a suspension of 1-adamantanamine hydrochloride (2.5 gm, 0.013 mol) in 50 ml of dry methylene chloride under a dry nitrogen atmosphere was added triethylamine (4.04 gm, 0.04 mol). The resulting solution was refluxed for thirty minutes, and then trichloromethyl chloroformate (1.32 gm, 0.0065 mol) was added dropwise and the resulting suspension was refluxed for three hours. The reaction mixture was then allowed to cool to room temperature and divided into two equal aliquots, each to theoretically contain 0.0065 mol of 1-adamantylisocyanate.

To one aliquot was added a solution of 2-[4-(2-primidyl)-1-piperazinyl]ethylamine (1.35 gm, 0.0065 mol) in 15 ml of dry methylene chloride, followed by an additional two equivalents of triethylamine (2.7 gm, 0.013 mol). The resulting mixture was allowed to stir at room temperature overnight. The reaction mixture was then diluted to 200 ml with methylene chloride, washed with 5% aqueous sodium bicarbonate solution, dried over anhydrous sodium sulfate, and concentrated on a rotary evaporator to yield a yellow oil. The title compound, as a hemihydrate (TLC on silica gel using a 20% methanol in ethyl acetate solvent mixture, Rf=0.41), was isolated by gravity chromatography on silica gel and recrystallized from methylene chloride/hexane (1.77 gm, 71% of theory), m.p.=170°-171° C.

Elemental Analysis for $C_{21}H_{32}N_6O \cdot \frac{1}{2}H_2O$: Calc'd: C, 64.09; H, 8.45; N, 21.35. Found: C, 64.52; H, 8.53; N, 21.11.

EXAMPLE 2

N-[2-[4-(2-methoxyphenyl)-1-piperazinyl]ethyl]-N'-tricyclo]3.3.1.1(3,7)]dec-1-ylurea To the second aliquot of 1-adamantylisocyanate produced in Example 1 was added a solution of 2-[4-(2-methoxyphenyl)-1-piperazinyl]ethylamine (1.55 gm, 0.0065 mol) in 15 ml of dry methylene chloride, followed by an additional two equivalents of triethylamine (1.35 gm, 0.013 mol). The resulting mixture was stirred at room temperature overnight. The reaction mixture was then diluted to 200 ml with methylene chloride, washed with 5% aqueous sodium bicarbonate solution, dried over anhydrous sodium sulfate, and concentrated on a rotary evaporator. The title compound, as a hydrate, (TLC on silica gel using a 20% methanol in ethyl acetate solvent system, Rf=0.51) was isolated by gravity chromatography on silica gel and recrystallized from methylene chloride/hexane (1.05 gm, 39% of theory), mp.=108°-110° C.

Elemental Analysis for $C_{24}H_{36}N_4O_2 \cdot H_2O$: Calc'd: C, 66.94; H, 8.89; N, 13.01. Found: C, 66.59; H, 8.86; N, 13.14.

EXAMPLE 3

N-[2-[4-(3-chlorophenyl)-1-piperazinyl]ethyl]-N'-tricyclo[3.3.1.1(3,7)]dec-1-ylurea To a stirred suspension of 1-adamantanamine hydrochloride (1.0 gm, 0.0053 mol) and triethylamine (2.2 gm, 0.021 mol) in 25 ml of dry methylene chloride under a dry nitrogen atmosphere was added, dropwise, trichloromethyl chloroformate (1.15 gm, 0.0027 mol). The resulting suspension was refluxed for three hours, and then a solution of 2-[4-(3-chlorophenyl)-1-piperazinyl]ethylamine (1.28 gm, 0.0053 mol) in 15 ml of dry methylene chloride was added. The resulting mixture was allowed to stir at room temperature overnight. The reaction mixture was then diluted to 200 ml with methylene chloride, washed with 3% aqueous sodium bicarbonate solution, dried over anhydrous sodium sulfate, and concentrated on a rotary evaporator. The title compound (TLC on silica gel using a 5% methanol in ethyl acetate solvent system, Rf=0.43) was isolated by preparatory high pressure liquid chromatography (HPLC) on silica gel (using a gradient consisting of from 10% ethyl acetate in hexane to 20% methanol in ethyl acetate) and recrystallized from methylene chloride/hexane (1.51 gm, 68% of theory), mp.=136°-137° C.

Elemental Analysis for $C_{23}H_{33}ClN_4O$: Calc'd: C, 66.25; H, 7.98; N, 13.44. Found: C, 66.10; H, 7.95; N, 13.29.

EXAMPLE 4

N-[3[4-(2-pyrimidyl)-1-piperazinyl]propyl]-N'-tricyclo[3.3.1.1(3,7)]dec-1-ylurea To a stirred suspension of 1-adamantanamine hydrochloride (1.25 gm, 0.0067 mol) and triethylamine (2.7 gm, 0.027 mol) in 25 mol of dry methylene chloride under a dry nitrogen atmosphere was added, dropwise, trichloromethyl chloroformate (1.33 gm, 0.0033 mol). The resulting suspension was refluxed for three hours, and then a solution of 3-[4-(2-pyrimidyl)-1-piperazinyl]propylamine (1.44 gm, 0.0067 mol) in 15 ml of dry methylene chloride was added. The resulting mixture was allowed to stir at room temperature overnight. The reaction mixture was then diluted to 200 ml with methylene chloride, washed with 3% aqueous sodium bicarbonate solution, dried over anhydrous sodium sulfate, and concentrated on a rotary evaporator. The title compound (TLC on silica gel using a 30% methanol in ethyl acetate solvent system, Rf=0.39) was isolated by gravity chromatography on silica gel and recrystallized from methylene chloride/hexane (1.76 gm, 60% of theory), mp.=172°-173° C.

Elemental Analysis for $C_{22}H_{34}N_6O$: Calc'd: C, 66.30; H, 8.60; N, 21.09. Found: C, 65.83; H, 8.46; N, 20.70.

EXAMPLE 5

N-[3-[4-(2-methoxyphenyl)-1-piperazinyl]propyl]-N'-tricyclo[3.3.1.1(3,7)]dec-1-ylurea To a stirred suspension of 1-adamantanamine hydrochloride (1.25 gm, 0.0067 mol) and triethylamine (2.7 gm, 0.027 mol) in 25 ml of dry methylene chloride under a dry nitrogen atmosphere was added, dropwise, trichloromethyl chloroformate (1.33 gm, 0.0033 mol). The resulting suspension was refluxed for three hours, and then a solution of 3-[4-(2-methoxyphenyl)-1-piperazinyl]propylamine (1.64 gm, 0.0067 mol) in 15 ml of dry methylene chloride was added. The resulting mixture was allowed to stir at room temperature overnight. The reaction mixture was then diluted to 200 ml with methylene chloride, washed with 3% aqueous sodium bicarbonate solution, dried over anhydrous sodium sulfate, and concentrated on a rotary evaporator. The title compound (TLC on silica gel using a 20% methanol in ethyl acetate solvent system, RF=0.35) was isolated by gravity chromatography on silica gel and recrystallized from methylene chloride/hexane (1.65 gm, 53% of theory), mp.=181°-182° C.

Elemental Analysis for $C_{25}H_{38}N_4O_2$: Calc'd: C, 70.39; H, 8.98; N, 13.13. Found: C, 69.99; H, 8.88; N, 13.10.

EXAMPLE 6

N-[3-[4-(3-chlorophenyl)-1-piperazinyl]propyl]-N'-tricyclo[3.3.1.1(3,7)]dec-1-ylurea To a stirred suspension of 1-adamantanamine hydrochloride (1.0 gm, 0.0053 mol) and triethylamine (2.2 gm, 0.021 mol) in 25 ml of dry methylene chloride under a dry nitrogen atmosphere was added, dropwise, trichloromethyl chloroformate (1.15 gm, 0.0027 mol). The resulting suspension was refluxed for three hours, and then a solution of 3-[4-(3-chlorophenyl)-1-piperazinyl]propylamine (1.35 gm, 0.0053 mol) in 15 ml of dry methylene chloride was added. The resulting mixture was allowed to stir at room temperature overnight. The reaction mixture was then diluted to 200 ml with methylene chloride, washed with 3% aqueous sodium bicarbonate solution, dried over anhydrous sodium sulfate, and concentrated on a rotary evaporator. The title compound (TLC on silica gel using a 20% methanol in ethyl acetate solvent system, Rf=0.42) was isolated by gravity chromatography on silica gel and recrystallized from methylene chloride/hexane (1.52 gm, 61% of theory), mp.=174°-175° C.

Elemental Analysis for $C_{24}H_{35}ClN_4O$: Calc'd: C, 66.88; H, 8.18; N, 13.00. Found: C, 66.33; H, 8.22; N, 12.97.

The compounds of this invention are antidepressant, anxiolytic agents useful in the treatment of depression and/or anxiety as a singular, primary mental problem as well as secondary, attending problems such as sexual dysfunction. Some of the compounds possess sufficient dopaminergic activity to be useful in treating psychoses such as schizophrenia or paranoia. Examples of compounds with sufficient limbic $D_2$ (dopamine) receptor affinity to be considered to have an antipsychotic parameter are those of Examples 3 and 5 which exhibited 56 and 66 percent inhibition of $^3$H-spiroperidol binding to limbic brain tissue at 1 μM concentration of the test compound. The $D_2$ receptor affinity of the compounds of this invention was determined by a modification of the test procedure of Fields et al., Brain Res. 136, 578 (1977) and Yamamura et al., eds., Neurotransmitter Receptor Binding, Raven Press, N.Y. (1978) as discussed in U.S. Pat. No. 4,636,563. The percentage reduction of $^3$H-spiroperidol binding at 1 μM concentration of test compound is reported, infra.

The serotoninergic properties of the compounds of this invention were established by the procedure of Hall et al., J. Neurochem. 44, 1685-1696 (1985) by demonstrating that representative compounds exemplified herein displace $^3$H-8-OH DPAT (dipropylaminotetralin) from the 5-HT$_{1A}$ serotonin receptor subtype. The results of this standard pharmacological procedure are reported, infra, as the percent inhibition at 1 μM or 100 nM concentration of test compound or by providing the inhibition constant Ki for the specific test compound where that calculation has been made from appropriate IC$_{50}$ values. Buspirone exhibits a Ki value of 10 nM (97% inhibition at 1 μM) in this test procedure.

| Affinity for 5-HT$_{1A}$ Receptor Sites | | |
|---|---|---|
| Compounds of Example | % Inhibition at 1 μM (Ki in nM) | % Inhibition at 100 nM |
| 1 | 91% (52 nM) | |
| 2 | 100% | |
| 3 | | 54% |
| 4 | 100% (7 nM) | |
| 5 | 100% | |
| 6 | 95% (45 nM) | |

| Affinity for D$_2$ Receptor Sites | |
|---|---|
| Compound of Example | % Inhibition at 1 μM |
| 1 | 15% |
| 2 | |
| 3 | 56% |
| 4 | 10% |
| 5 | 66% |
| 6 | 38% |

In qualitatively evaluating the above data, high affinity values for 5-HT$_{1A}$ receptors correlate (by analogy with buspirone) with anxiolytic-antidepressant activity, while lower values reflect a lesser activity. High affinity values for $D_2$ receptor binding begin to show some antipsychotic activity.

Hence, the compounds of this invention are antidepressant/anxiolytic agents useful in the treatment of depression and in alleviating anxiety and in the case of the products of Examples 3 and 5, they have some meaningful antipsychotic activity which is useful in the treatment of psychoses such as paranoia and schizophrenia. As such, the compounds of this invention may be administered to a patient in need thereof, either neat or with a conventional pharmaceutical carrier. The pharmaceutical carrier may be solid or liquid as suitable for oral or parenteral administration.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is subdivided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or table itself, or it can be the appropriate number of any such compositions in package form.

The dosage to be used in the treatment of anxiety, depression, psychosis, etc. must be subjectively determined by the attending physician. The variables involved include the specific state of depression, anxiety or psychoses and the size, age and response pattern of the patient.

What is claimed is:

1. A compound of the formula:

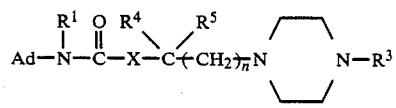

wherein
Ad is 1-adamantyl, 2-adamantyl or 3-noradamantyl;

X is —O— or

n is 1, 2, 3 or 4;

R[1] and R[2] are, independently, hydrogen, alkyl of 1 to 3 carbon atoms, phenyl, benzyl, or substituted phenyl or benzyl in which the substituent is alkyl of 1 to 3 carbon atoms, alkoxy of 1 to 3 carbon atoms, halo, cyano, nitro or trifluoromethyl;

R[3] is phenyl, benzyl or substituted phenyl or benzyl in which the substituent is alkyl of 1 to 3 carbon atoms, alkoxy of 1 to 3 carbon atoms, halo, nitro, cyano or perhalomethyl, 2-, 3-, or 4-pyridinyl, 2-, 4- or 5-pyrimidinyl or 2- or 3-pyrazinyl;

and

R[4] and R[5] are, independently, hydrogen, methyl, phenyl or benzyl; or a pharmaceutically acceptable salt thereof.

2. A compound of claim 1 in which Ad is 1-adamantyl.

3. A compound of claim 1 which is N-[2-[4-(2-pyrimidyl)-1-piperazinyl]ethyl-N'-tricyclo[3.3.1.1(3,7)]-dec-1-ylurea, or a pharmaceutically acceptable salt thereof.

4. A compound of claim 1 which is N-[2-[4-(2-methoxyphenyl)-1-piperazinyl]ethyl]-N'-tricyclo]3.3.1.1(3,7)]dec-1-ylurea, or a pharmaceutically acceptable salt thereof.

5. A compound of claim 1 which is N-[2-[4-(3-chlorophenyl)-1-piperazinyl]ethyl]-N'-tricyclo[3.3.1.1(3,7)]-dec-1-ylurea, or a pharmaceutically acceptable salt thereof.

6. A compound of claim 1 which is N-[3-[4-(2-pyrimidyl)-1-piperazinyl]propyl-N'-tricyclo[3.3.1.1(3,7)]dec-1-ylurea, or a pharmaceutically acceptable salt thereof.

7. A compound of claim 1 which is N-[3-[4-(2-methoxyphenyl)-1-piperazinyl]propyl]-N'-tricyclo[3.3.1.1(3,7)]dec-1-ylurea, or a pharmaceutically acceptable salt thereof.

8. A compound of claim 1 which is N-[3-[4-(3-chlorophenyl)-1-piperazinyl]propyl]-N'-tricyclo[3.3.1.1(3,7)]-dec-1-ylurea, or a pharmaceutically acceptable salt thereof.

* * * * *